(12) United States Patent
Solanki et al.

(10) Patent No.: US 8,841,442 B2
(45) Date of Patent: Sep. 23, 2014

(54) PROCESS FOR PREPARING FLUTICASONE PROPIONATE/FUROATE

(75) Inventors: Kirtipalsinh Solanki, Ahmedabad (IN); Ruchir Z Bavadia, Ahmedabad (IN); Dhaval P Patel, Ahmedabad (IN); Dhaval J Patel, Ahmedabad (IN); Tejash C Shah, Ahmedabad (IN); Manoj Kumar Singh, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 13/820,124

(22) PCT Filed: Sep. 2, 2011

(86) PCT No.: PCT/IN2011/000600
§ 371 (c)(1),
(2), (4) Date: May 14, 2013

(87) PCT Pub. No.: WO2012/029077
PCT Pub. Date: Mar. 8, 2012

(65) Prior Publication Data
US 2014/0148593 A1      May 29, 2014

(30) Foreign Application Priority Data
Sep. 1, 2010   (IN) .................. 2430/MUM/2010

(51) Int. Cl.
*C07J 31/00* (2006.01)
*C07J 75/00* (2006.01)
*C07J 41/00* (2006.01)

(52) U.S. Cl.
CPC ............... *C07J 31/00* (2013.01); *C07J 31/006* (2013.01); *C07J 41/005* (2013.01)
USPC ........................... 540/114; 552/610; 552/622

(58) Field of Classification Search
USPC .................... 540/114; 552/610, 622
See application file for complete search history.

(56) References Cited

U.S. PATENT DOCUMENTS 4,335,121 A    6/1982  Phillipps et al.
2006/0009435 A1  1/2006  Kaspi

FOREIGN PATENT DOCUMENTS

WO    0212265 A1    2/2002
WO    2004001369 A2   12/2003

OTHER PUBLICATIONS

Malanga, Franco et al; "Process for the Preparation of Androstadienecarbothioates", Chemical Abstracts Service, Mar. 20, 2006, page Nos. 1-2.
Phillipps G. H. et al; "Synthesis and Structure-Activity Relationships in a Series of Antiinflammatory corticosteroid analogues", Journal of Medicinal Chemistry, American Chemical Society, vol. 37, No. 22, Oct. 1, 1994.
European Patent Office Acting As the International Search Authority, "International Search Report", PCT/IN2011/000600, Mar. 8, 2012.
European Patent Office Acting As the International , "International Preliminary Report on Patentability", PCT/IN2011/000600, Feb. 25, 2013.

*Primary Examiner* — Brenda Coleman
(74) *Attorney, Agent, or Firm* — Iphorgan Ltd.

(57) ABSTRACT

The present invention relates to an improved process for the preparation of substituted Fluticasone derivatives. The invention also reveals the processes for the purification of Fluticasones and related intermediates to provide the highly pure product.

7 Claims, 2 Drawing Sheets

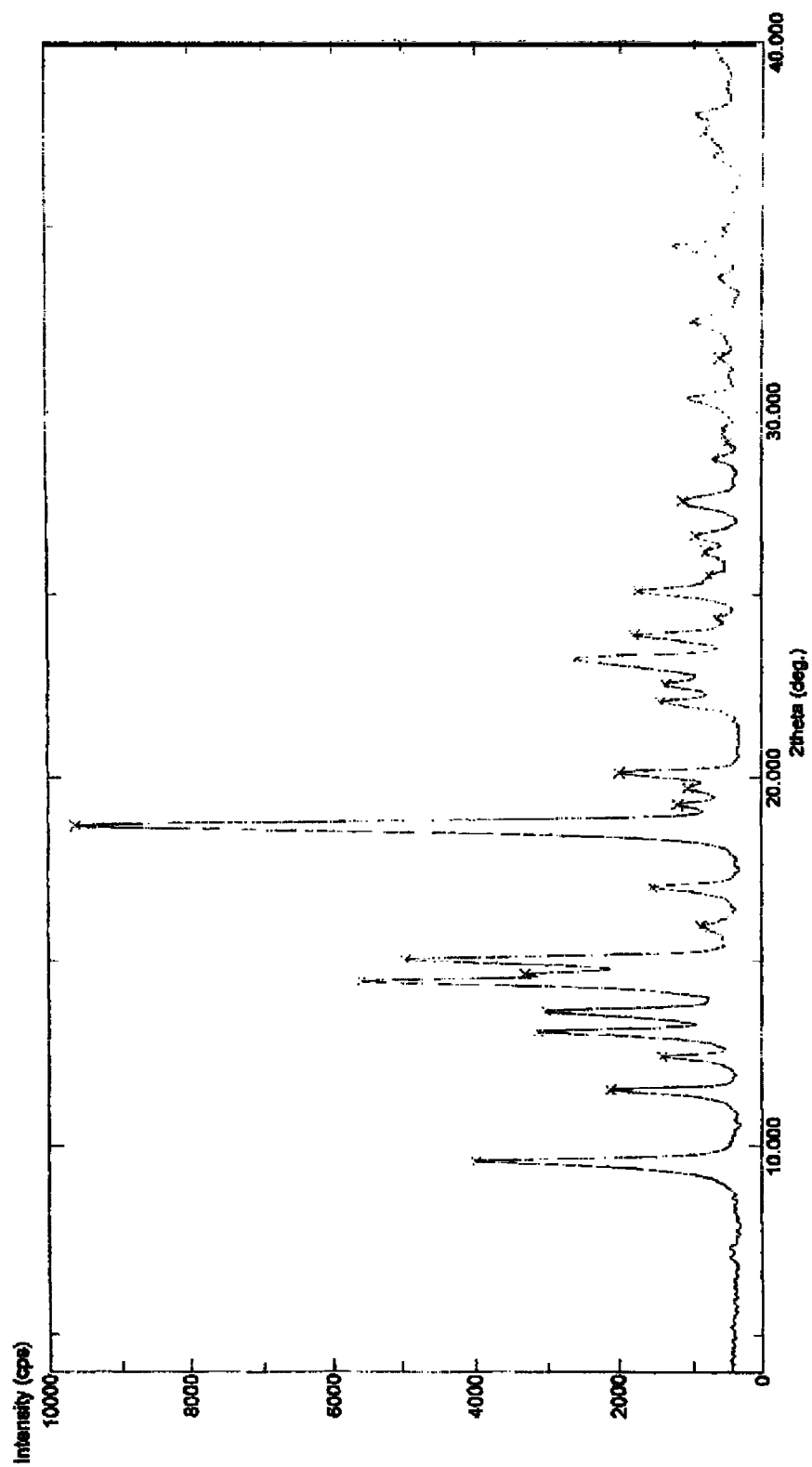

PROCESS FOR PREPARING FLUTICASONE PROPIONATE/FUROATE

FIELD OF INVENTION

The invention relates to an improved process for the preparation of Fluticasone propionate/furoate. The invention also relates to a process for the purification of Fluticasone propionate/furoate and an intermediate of formula 6. The invention also relates to the use of pure intermediate of formula 6 for the preparation of Fluticasone propionate/furoate.

BACKGROUND ART

Fluticasone propionate (R—$CH_2CH_3$)/furoate (2-furyl) of formula 1, chemically known as S-fluoromethyl-6α,9α-difluoro-11β-hydroxy-16α-methyl-17α-propionyloxy-3-oxo-androsta-1,4-diene-17β-carbothioate (1a) and S-fluoromethyl-6α,9α-difluoro-11β-hydroxy-16α-methyl-17α-(2-furoyloxy)-3-oxo-androsta-1,4-diene-17β-carbothioate (1b), are members of the corticosteroidal androstane 17β-thioic acid fluoromethyl ester family and a synthetic steroid of the glucocorticoid family. The naturally occurring hormone, cortisol or hydrocortisone, is produced by the adrenal glands. Glucocorticoid steroids have potent anti-inflammatory actions. When used as a nasal inhaler or spray, the medication goes directly to the inside lining of the nose and very little is absorbed into the rest of the body.

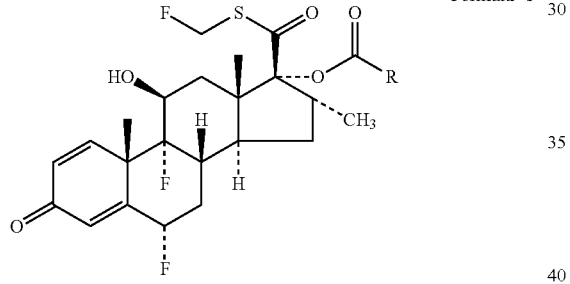

Formula -1 a) R = $CH_2CH_3$
b) R = 2-Furyl

U.S. Pat. No. 4,335,121 discloses the compound of formula 1a [Fluticasone propionate (R—$CH_2CH_3$)] and its preparation. It discloses the process of its preparation by treating 6α,9α-di fluoro-11β-hydroxy-16α-methyl-3-oxo-17α-(propionyloxy)androsta-1,4-dien-17β-carboxylic acid, a compound of formula 4a with dimethylthiocarbamoyl chloride to yield 17β-[(N,N-dimethylcarbamoyl)thio]carbonyl-6α,9α-difluoro-11(3-hydroxy-16α-methyl-17β-propionyloxy-3-oxoandrosta-1,4-diene, a compound of formula 5a, which is decomposed by refluxing in diethylamine to the thioic acid of formula 6a. The compound of formula 6a is then reacted with bromochloromethane in presence of sodium bicarbonate to give a chloromethyl ester of formula 7a. The compound of formula 7a, is converted to an iodomethyl ester by halogen exchange and subsequently treated with silver fluoride to yield the compound of formula 1a. This process of preparation of the compound of formula 1a is very tedious, lengthy, and involves use of expensive and sensitive chemicals, viz. silver fluoride. This prior art teaches the use of ammonia, a primary amine or more preferably a secondary amine such as diethylamine or pyrrolidine for conversion of compound of formula 5a to compound of formula 6a. However, the yield obtained with use of secondary amines such as diethylamine is poor.

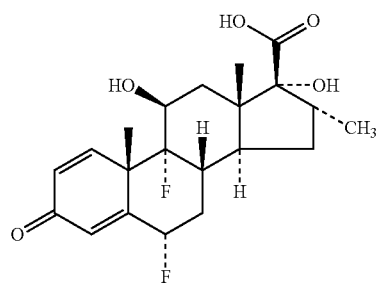

Formula - 2

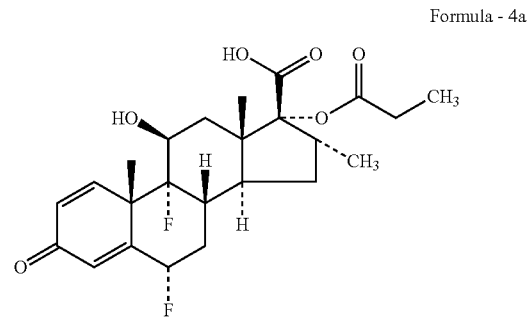

Formula - 4a

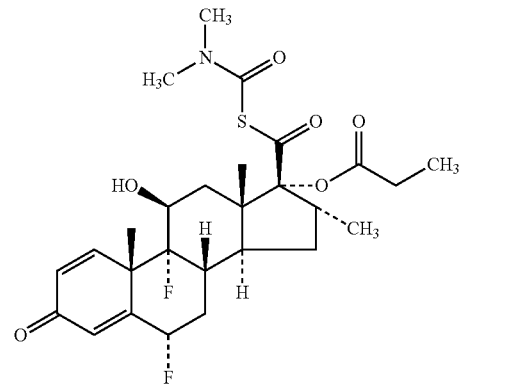

Formula - 5a

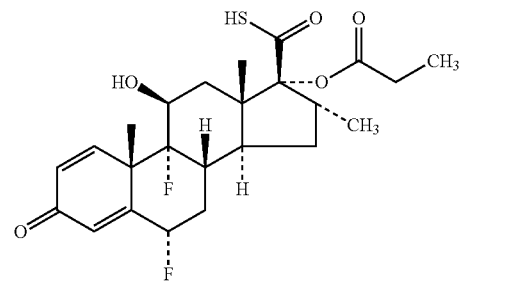

Formula - 6a

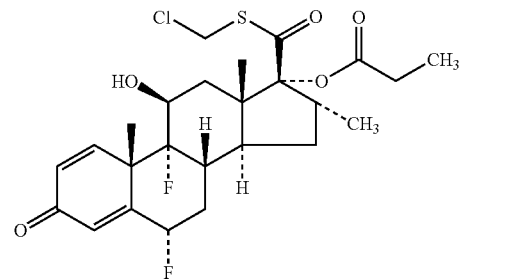

Formula - 7a

Formula - 8

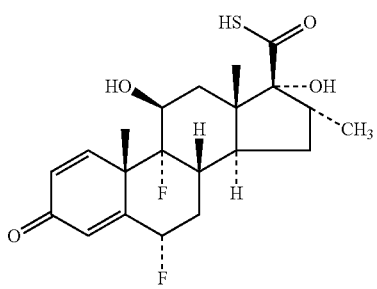

WO 01/62722 discloses the method of preparing the compound of formula 1a by reacting a compound of formula 4a with dimethylthiocarbamoyl chloride and molar equivalents of sodium iodide in 2-butanaone to get compound of formula 5a. The compound of formula 5a is then reacted with a hydrolyzing agent such as sodium hydrosulfide to generate the sodium salt of formula 6a, which can be alkylated in-situ with chlorofluoromethane to yield the compound of formula 1a or alternately can be acidified to obtain the compound of formula 6a, which can be isolated and converted to compound of formula 1a by alkylation with chlorofluoromethane. This prior art publication teaches the use of an alkoxide salt, a thioalkoxide salt or a hydrated sulfide salt for hydrolyzing the compound of formula 5a to obtain the corresponding thiocarboxylic acid, the compound of formula 6a. The use of sodium hydrosulfide hydrate or sodium thiomethoxide as hydrolyzing agent for conversion of 17β-carboxylic acid to 17β-carbothioic acid, via the intermediacy of 17β-[(N,N-dimethylcarbamoyl)thio]carbonyl derivative, has been exemplified. However, sodium thiomethoxide is a corrosive and moisture sensitive reagent and use of sodium thiomethoxide would generate toxic methyl mercaptan during acidification and sodium hydrosulfide is unstable and converts to sodium thiosulfate and sodium carbonate upon storage. In the in-situ alkylation of sodium salt of compound of formula E, the excess sodium hydrosulfide would react with the chlorofluoromethane generating toxic and obnoxious organosulfur byproducts, which can pose health hazards. Although isolation of thioic acid of formula 6a can be performed (by treatment with an acid) to overcome the problem, the excess sodium hydrosulfide would generate toxic hydrogen sulfide. Further, the thiosulfate impurity which is invariably present in sodium hydrosulfide, would generate sulfur upon acidification, which would contaminate the thioic acid and whose removal would pose difficulties.

Gordon H. Phillipps et al, Journal of Medicinal Chemistry 37, 3717-3729 (1994), disclose the method of preparing the compound of formula 1a by treating a compound of formula 2 with carbonyldiimidazole under nitrogen, followed by a reaction with hydrogen sulfide to give the thioic acid of formula 8, which is isolated and treated with propionyl chloride to give the compound of formula 6a. This compound is then alkylated with bromofluoromethane under nitrogen to yield the compound of formula 1a in 69.3% yield.

This reference does not mention the preparation of compound of formula 1a directly from the compound of formula 5a. IL Patent No. 109656 discloses preparation of fluticasone propionate by esterification of compound of formula 6a with a halofluoromethane, optionally in the presence of a catalyst such as tetrabutylammonium bromide.

The process described in international patent application WO 2004/001369 comprising the 17β-N,N-dimethylthiocarbamoyloxycarbonyl compound 5a was treated with an alkali metal carbonate-alcohol system, for example potassium carbonate in methanol, to obtain the alkali metal salt of compound 6a (6α,9α-difluoro-11β-hydroxy-16α-methyl-17α-propionyloxy-3-oxo-androsta-1,4-diene-17β-carbothioate sodium). Alkali metal salt was treated in situ with bromofluoromethane to obtain fluticasone propionate 1a. Alternatively, compound 6a was isolated by acid treatment and then reacted with bromofluoromethane to obtain fluticasone propionate 1a. Alternatively still, thiocarbamate 5a was reacted with a hydrosulphide reagent, such as sodium hydrosulphide, and bromofluoromethane to obtain fluticasone propionate 1a. Hence, this process also uses bromofluoromethane, which raises environmental concerns.

EP 1431305 also described a process for the preparation of fluticasone propionate 1a, a drawback associated with this process is the oxidative dimerisation of the sulphur compounds to give dimer impurities especially under pressure or with long reaction times. Such by-products are formed in significant amounts, which are difficult to control/reduce within the limits of stringent pharmacopoeial specifications even after multiple purifications.

A process disclosed by Farmabios in international patent application WO 2004/052912 used a different approach, shown in scheme 1, for the conversion of organic amine salt 6 to fluticasone propionate 1a. Amine salt 9a was hydroxymethylated using formaldehyde to give alcohol 10a (S-hydroxymethyl-6α,9α-difluoro-11β-hydroxy-16α-methyl-17α-propionyloxy-3-oxo-androsta-1,4-diene-17β-carbothioate). This intermediate 10a was selectively fluorinated using bis(2-methoxyethyl)aminosulphur trifluoride (Deoxo-Fluor®), diethylaminosulphur trifluoride (DAST®), or hexafluoropropyldiethylamine (MEC-81®), to obtain fluticasone propionate 1a.

SCHEME 1

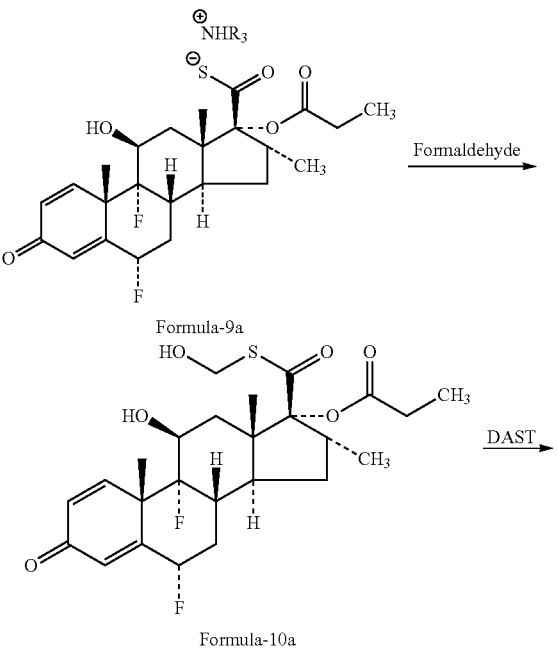

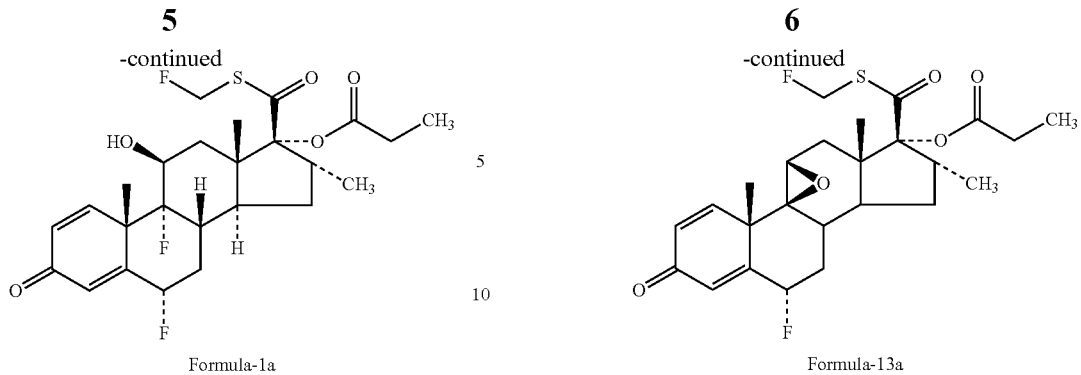

Formula-1a

Formula-13a

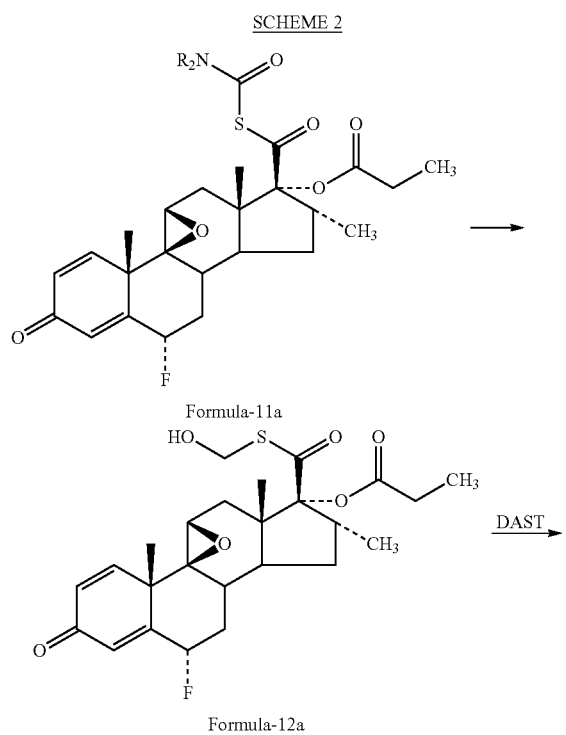

Formula-1a

WO 2004/052912 also discloses a minor modification of the process described in scheme 2. In the modified process, depicted in scheme 2, 17β-N,N-dimethylthiocarbamoyloxycarbonyl-9β,11β-epoxy-6α-fluoro-17α-propionyloxy-16α-methyl-3-oxo-androsta-1,4-diene 11a was converted to S-hydroxymethyl-9β,11β-epoxy-6α-fluoro-17α-propionyloxy-16α-memyl-3-oxo-androsta-1,4-diene-carbothioate 12a. Intermediate 12a was further converted into S-fluoromethyl-9β,11β-epoxy-6α-fluoro-17α-propionyloxy-16α-methyl-3-oxo-androsta-1,4-diene-carbothioate 13a using DAST®. Fluticasone propionate 1a was then obtained by the opening of the epoxide of compound 13a using hydrofluoric acid. The use of hazardous DAST as a fluorinating agent and the use of highly corrosive hydrofluoric acid are major disadvantages of this process described in WO 2004/052912.

SCHEME 2

Formula-11a

Formula-12a

WO0212265 discloses a 6α,9α-difluoro-17α-[(2-furanylcarbonyl)oxy]-11α-hydroxy-16α-methyl-3-oxo-androsta-1,4-diene-17β-carbothioic acid S-fluoromethyl ester (Fluticasone furoate) of formula 1b and a process for preparing this compound which are common with intermediates in the synthesis of a compound of formula 1a (R—CH$_2$CH$_3$) are described in U.S. Pat. No. 4,335,121.

WO2002012265 discloses the compound of formula 1b (Fluticasone furoate (R-2-furyl) and its preparation. WO03013427 disclosed the process for the preparation of the compound of formula 1b (Fluticasone furoate (R-2-furyl) comprises reacting compound of formula 6b (R-2-furyl), with chlorofluoro methane and mild base.

WO2007144363 disclosed the process for the preparation of the compound of formula 1b (Fluticasone furoate (R-2-furyl) comprises reacting carbothioic acid with 2-furancarbonyl chloride using DMAP and Et$_3$N in MeCOEt at 20-22° C. under a N$_2$ atm. for 10 min, treatment of the resulting thioanhydride (R=2-furanylcarbonyl) with a solution of N-methylpiperazine in H$_2$O added drop wise of t 2-3 min at −5-10° C., and finally, reacting the resulting carbothioic acid (R=2-furanylcarbonyl) with BrCH$_2$F in methyl ethyl ketone at 20-22° C. for 5 hrs.

WO0208243 discloses processes for preparing intermediates useful in the preparation of Fluticasone propionate and Fluticasone furoate.

Like any synthetic compound, Fluticasone propionate/furoate can contain extraneous compounds or impurities that can come from many sources. They can be unreacted starting materials, by-products of the reaction, and products of side reactions or degradation products. Impurities in compound of formula 6 as in its active pharmaceutical ingredient (API), Fluticasone propionate/furoate, are undesirable and might even be harmful to a patient being treated with a dosage form containing the API.

The purity of the API produced in the commercial manufacturing process is clearly a necessary condition for commercialization. Impurities introduced during commercial manufacturing processes must be limited to very small amounts, and are preferably substantially absent. For example, the International Conference on Harmonisation of Technical Requirements for Registration of Pharmaceuticals for Human Use ("ICH") Q7A guidance (dated Nov. 10, 2000) for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of compound of formula 6 or during the processing of an API, such as Fluticasone propionate/furoate, it must be analyzed for purity, typically, by HPLC or TLC analysis, to determine if it is suitable for continued processing and, ultimately, for use in a pharmaceutical product. The compound of formula 6 or API need not be absolutely pure, as absolute purity is a theoretical ideal that is typically unattainable. Rather, purity standards are set with the intention of ensuring that an API is as free of impurities as possible, and thus, are as safe as possible for clinical use. As discussed above, in the United States, the Food and Drug Administration guidelines recommend that the amounts of some impurities be limited to less than 0.1 percent.

Thus, providing highly pure compound of formula 6 and means for the preparation thereof is desirable.

Thus the prior art processes described above for the synthesis of fluticasone propionate/furoate (I) suffer from various limitations with respect to process parameters, yields, purity and quality, as well as serious environmental issues. In view of these drawbacks, there is a need for an improved process for the preparation of fluticasone propionate/furoate (I), which addresses the limitations associated with the prior art processes.

In view of the various drawbacks in the prior arts, a suitable reagent for the hydrolysis of N,N-dimethylthiocarbonyl group in formula 5 was required to get the compound of formula 6 in high yield and quality. In order to explore the suitable base various bases and solvent systems are tried to get compound of formula 6 in pure form and we observed that use of cyclic amines afford best quality with increased yield of the product.

The object of the present invention is to provide a facile, efficient and economic process for the preparation of better quality of Fluticasone 17α-ester derivatives. The use of various reagents and solvents were explored during the course of the exploration of the process. The present invention provides a convenient process for preparation of compound of formula 1, wherein various secondary amines are explored for the conversion of a compound of formula 5 to a compound of formula 6 in contrast to prior art. Different solvents and mixture of solvents are used for the purification of compound of formula 6, and the compound of formula 1 is treated with a various solvents or a mixture of solvents. The advantages include an improved yield, use of reagents that are easy to handle, low reaction time and use of lesser molar amounts of the reagents with the highest purity of product.

SUMMARY OF THE INVENTION

In particular, the present invention provides a convenient economical process for preparation of high quality of compound of formula 1, wherein cyclic amines are used for the conversion of a compound of formula 5 to a compound of formula 6 which is subsequently converted to compound of formula 1. The use of cyclic amines provides high yields of compound of formula 1 with improved quality of product. In an embodiment is provided a process for the purification of compound of formula 6, which decreases the possibility of the presence impurities in the compound of formula 6 and to reduce the possibility of formation of other related substances in the compound of formula 1. The advantages of the present process includes an improved yield, use of reagents that are easy to handle, low reaction time and use of lesser molar amounts of the reagents with the highest purity of product.

In an embodiment is provided a process for purification of compound of formula 1, wherein the compound of formula 1 is treated with an aprotic solvent or a mixture of solvents optionally using water as mixture. This purification removes traces of the unknown impurity referred to in the European Pharmacopeia. The advantages include an improved yield, use of reagents that are easy to handle, low reaction time and use of lesser molar amounts of the reagents with the highest purity of product.

BRIEF DESCRIPTION OF THE DRAWINGS

FIG. 2 is a powder X-ray diffraction (XRPD) pattern of Fluticasone Fuorate of compound of Formula 1b according to the present invention

DETAILED DESCRIPTION OF THE INVENTION

Figure 1:
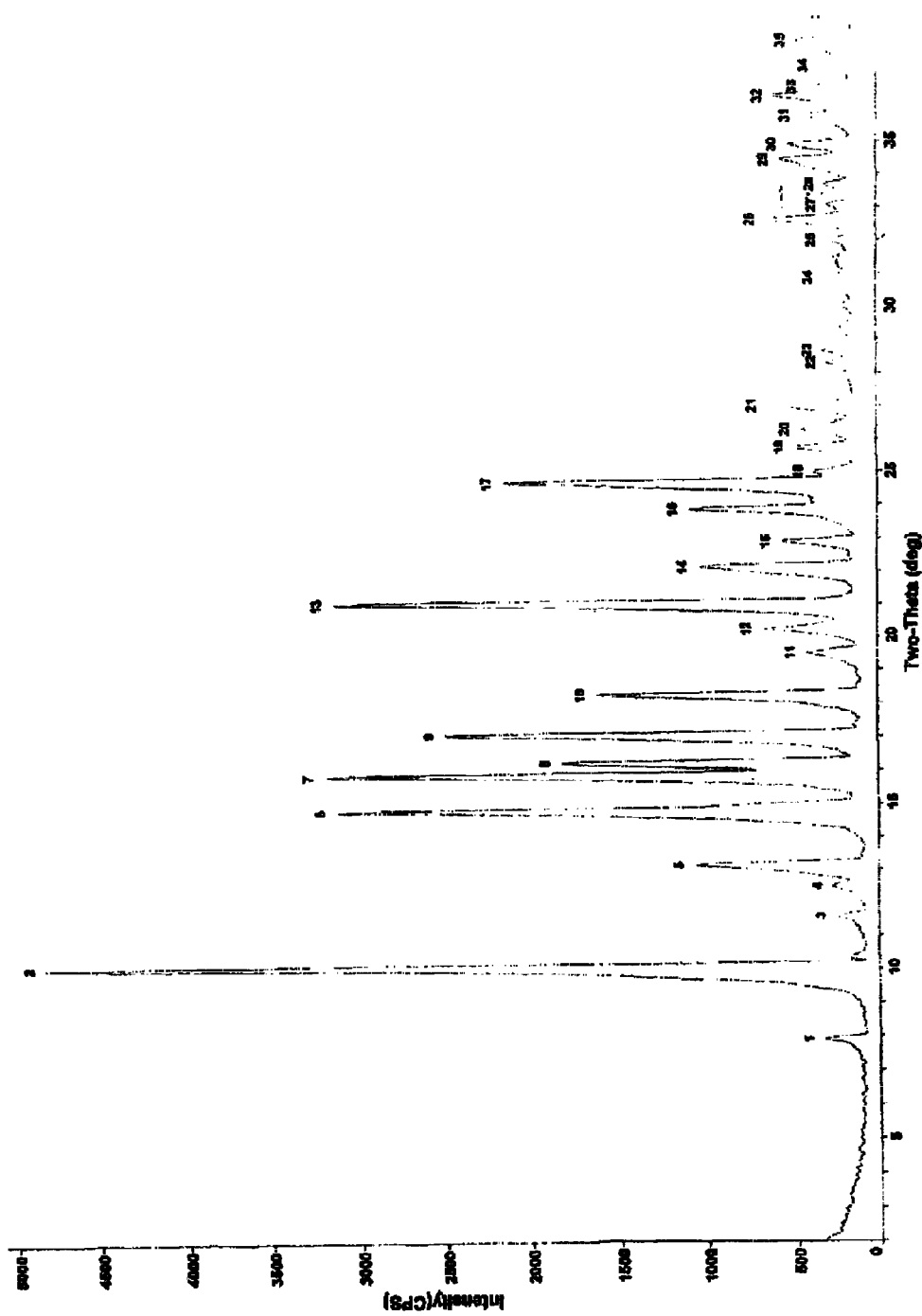
FIG. 1 is a powder X-ray diffraction (XRPD) pattern of Fluticasone Propionate of compound of Formula 1a according to the present invention

Accordingly, the invention provides a process for the preparation of Fluticasone propionate/furoate of the formula (I) is depicted below in Scheme 3: We have found a facile, efficient and economic process for the preparation of Compound of formula 1 (wherein R=$CH_2CH_3$ and 2-furyl) that provides an improved yield of the compound, using reagents that are easy to handle, utilizing a low reaction time and using the reagents in lesser molar amounts.

In one aspect the present invention provides a process for the preparation of a compound of formula 1, comprising (a) treating the compound of formula 5 with a cyclic secondary amine to obtain the compound of formula 6; (b) reacting the compound of formula 6 with bromofluoromethane to obtain the compound of formula 1; (c) further purification of crude compound of formula 1 with suitable solvents to get compound of formula 1 is desired purity.

SCHEME 3

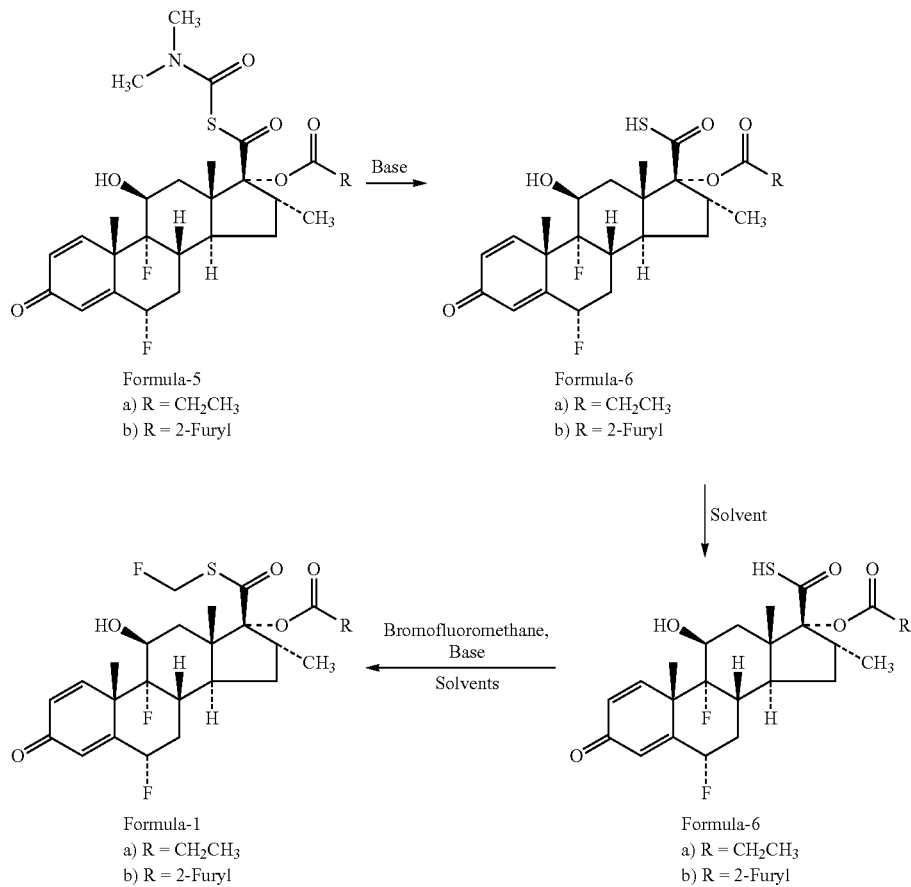

Formula-5
a) R = CH$_2$CH$_3$
b) R = 2-Furyl

Formula-6
a) R = CH$_2$CH$_3$
b) R = 2-Furyl

Formula-1
a) R = CH$_2$CH$_3$
b) R = 2-Furyl

Formula-6
a) R = CH$_2$CH$_3$
b) R = 2-Furyl

The compound of formula 5 is obtained by methods known in the art. In an embodiment, the term hydrocarbons used anywhere in the specification, unless otherwise specified means suitable hydrocarbons, more preferably those that are selected from benzene, toluene, xylene, ethyl benzene, trimethyl benzene and suitable mixtures thereof.

In an embodiment, the term alcohols used anywhere in the specification, unless otherwise specified means suitable (C$_1$-C$_{10}$) linear or branched chain alcohols, more preferably those that are selected from methanol, ethanol, isopropanol or suitable mixtures thereof.

In an embodiment, the term halogenated hydrocarbons, used anywhere in the specification, unless otherwise specified means suitable halogenated hydrocarbons, more preferably those that are selected from chloroform, dichloromethane, dichloroethane or suitable mixtures thereof.

In an embodiment, the term ketones, used anywhere in the specification, unless otherwise may be selected from acetone, methyl ethyl ketones, methyl isobutyl ketones or suitable mixtures thereof.

In an embodiment, the term cyclised and non-cyclised ethers, used anywhere in the specification, unless otherwise specified may be selected from as diisopropyl ether, methyl t-butyl ether, tetrahydrofuran, dioxanes or suitable mixtures thereof.

In an embodiment, the term amides, used anywhere in the specification, unless otherwise specified may be selected from dimethyl acetamides, dimethylformamide, N-methyl-2-pyrrolidinone or suitable mixtures thereof.

In an embodiment, the term aprotic polar solvents, used anywhere in the specification, unless otherwise specified may be selected from dimethyl sulfoxides.

In an embodiment, the term esters, used anywhere in the specification, unless otherwise specified may be selected from ethyl acetate, isopropyl acetate, butyl acetate or suitable mixtures thereof.

In particular, the present invention provides a convenient economical process for preparation of high quality of compound of formula 1, wherein cyclic amines are used for the conversion of a compound of formula 5 to a compound of formula 6. The use of cyclic amines provides high yields with improved quality of product.

The suitable bases in conversion of a compound of formula 5 to a compound of formula 6 are selected from heterocyclic saturated or unsaturated amines, preferably morpholine, piperidine, pyrollidine and pyridine & the like either independently or in suitable mixtures thereof.

Out of the above mentioned bases Morpholine provided best results as it undergoes most chemical reactions typical for other secondary amines.

The present invention also provides a purification process for the compound of formula 6, which decreases the possibility of the presence impurities in the compound of formula 6 and to reduce the possibility of formation of other related substances in the compound of formula 1. The advantages include an improved yield, use of reagents that are easy to handle, low reaction time and use of lesser molar amounts of the reagents with the highest purity of product.

The suitable solvent(s) used for the purification of the compound of formula 6, are selected from suitable hydrocarbons such as benzene, toluene, xylene, ethyl benzene, trimethyl benzene and the like; esters such as ethyl acetate, isopropyl acetate, butyl acetate and the like, halogenated hydrocarbon solvents such as chloroform, dichloromethane, dichloroethane and the like; ketones such as acetone, methyl ethyl ketones, methyl isobutyl ketones & the like; amides such as N,N-dimethyl acetamides, dimethylformamide, N-methyl-2-pyrrolidinone & the likes and ($C_1$ to $C_{10}$) alcohols such as methanol, ethanol, isopropanol & the like either independently or suitable mixtures thereof.

In one of the preferred embodiments the invention discloses the purification of compound of formula 6, preferably compound of formula 6a (wherein R represents $CH_2CH_3$) with a mixture of solvents such as methyl ethyl ketone, toluene and ethyl acetate, to remove undesired impurities from the product, which further leads to the removal of the unknown specified impurity, which has European Pharmacopeia limit of 0.2% (RRT in European Pharmacopeia HPLC Method: 1.23). This unknown impurity is thereinafter not present in the final product also leading to a purer product.

In another aspect the present invention relates to the condensation of compound of formula 6 with bromofluoromethane in the presence of suitable base and in suitable solvent(s) optionally adding water to the reaction mixture to isolate the product followed optionally by further purification of the reaction mass using suitable solvents(s) to provide compound of formula 1 with high yield and quality.

The suitable solvent(s) used for the conversion of compound of formula 6 to compound of formula 1 are selected from ketones such as acetone, methyl ethyl ketones, methyl isobutyl ketones & the like; nitriles such as acetonitrile; and water either independently or suitable mixtures thereof.

The suitable bases used for the conversion of compound of formula 6 to compound of formula 1 are selected from suitable inorganic bases such as carbonates such as $Na_2CO_3$, $K_2CO_3$, bicarbonates such as $NaHCO_3$, $KHCO_3$, and suitable organic bases are selected from cyclised and non-cyclised suitable organic bases such as $C_{1-5}$ alkyl amines, $C_{1-5}$ substituted alkyl amines preferably, diethyl amine, triethyl amine (TEA), diisopropyl amine, diisopropylethyl amine, heterocyclic saturated or unsaturated amines, preferably morpholine, piperidine, pyrollidine and pyridine and the like either independently or in suitable mixtures thereof.

The present invention provides an improved process for purification of compound of formula 1, wherein the compound of formula 1 is treated with an aprotic solvent or a mixture of solvents optionally using water as mixture. The advantages include an improved yield, use of reagents that are easy to handle, low reaction time and use of lesser molar amounts of the reagents with the highest purity of product.

The suitable solvent(s) used for the purification of compound of formula 1 are selected from suitable esters such as ethyl acetate, isopropyl acetate, butyl acetate and the like, halogenated hydrocarbon solvents such as chloroform, dichloromethane, dichloroethane and the like; ketones such as acetone, methyl ethyl ketones, methyl isobutyl ketones and the like; amides such as N,N-dimethyl acetamides, dimethylformamide, N-methyl-2-pyrrolidinone & the likes and ($C_1$ to $C_{10}$) alcohols such as methanol, ethanol, isopropanol & the like and water either independently or suitable mixtures thereof.

It will be appreciated that the process described above, with suitable modifications, alternations which are within the scope of a skilled person can be used for obtaining both Fluticasone propionate (R=$CH_2CH_3$) as well as Fluticasone furoate (R=2-furoate).

The process is further described by the following non-limiting examples, which provides the preferred mode of carrying out the process of the present invention. It is to be appreciated that several alterations, modifications, optimizations of the processes described herein are well within the scope of a person skilled in the art and such alterations, modifications, optimizations etc. should be construed to be within the scope of the present inventive concept as is disclosed anywhere in the specification.

EXAMPLE-1

6α,9α[-Difluoro-11β,17α-dihydroxy-16α-methyl-3-oxoandrosta-1,4-diene-17β-carboxylic acid A solution of sodium metaperiodate (78 g) in water (312 mL) was prepared by at 50-55° C. and then cool down to ambient temperature. This solution was added drop wise to a stirred suspension of flumethasone (100 g) in tetrahydrofuran (500 mL) at room temperature. After the addition was completed the mixture was stirred for further 2 hrs at 25-30° C. and thereafter quenched by addition of water. The precipitated solid mass was filtered and further washed with water (1 L) and dried at 70-75° C. Yield: 92.0 g (95.83%), HPLC Purity: 99%.

EXAMPLE-2

6α,9α-Difluoro-11β-hydroxy-16α-methyl-17α-propionyloxy-3-oxoandrosta-1,4-diene-17β-carboxylic acid A suspension of 6α,9α-difluoro-11β,17α-dihydroxy-16α-methyl-3-oxoandrosta-1,4-diene-17β-carboxylic acid (100 g) and triethyl amine (58.6 g) in acetone (500 mL) was cooled to 0-5° C., Another solution of propionyl chloride (49 g) in acetone (100 mL) was added to it drop wise in 1 hr and the reaction mixture was further stirred for 2 hr at 0-5° C. The reaction mixture was warmed up to 40-45° C. and diethyl amine (38 g) was added drop wise within 30 minutes. The reaction mixture was further stirred for 2 hr at 40-45° C., then cool down to 20-25° C. To the reaction mixture water was added slowly for 30 minutes and the reaction mixture was acidified to pH 1.5-2 by the addition of Conc. HCl and further stirred for 45 min. The precipitated solid product is filtered, washed with water, and dried at 70-75° C. Yield: 110 g (96.5%), HPLC Purity: 99%.

EXAMPLE-3

6α,9α-Difluoro-11β-hydroxy-16α-methyl-17α-propionyloxy-3-oxoandrosta-1,4-diene-17β-carboxylic acid A suspension of 6α,9α-difluoro-11β,17α-dihydroxy-16α-methyl-3-oxoandrosta-1,4-diene-17β-carboxylic acid (100 g) and diethanol amine (58.6 g) in acetone (500 mL) was cooled to 0-5° C., Another solution of propionyl chloride (49 g) in acetone (100 mL) was added to it drop wise in 1 hr and the reaction mixture was further stirred for 2 hr at 0-5° C. The reaction mixture was warmed up to 40-45° C. and diethyl amine (38 g) was added drop wise within 30 minutes. The reaction mixture was further stirred for 2 hr at 40-45° C., then cool down to 20-25° C. To the reaction mixture water was added slowly for 30 minutes and the reaction mixture was acidified to pH 1.5-2 by the addition of Conc. HCl and further stirred for 45 min. The precipitated solid product is filtered, washed with water, and dried at 70-75° C. Yield: 100 g (96.5%), HPLC Purity: 94%.

EXAMPLE-4

17β-[(N,N-Dimethylcarbornyl)thio]-6α,9α-difluoro-11β-hydroxy-16α-methyl-17α-propionyloxy-3-oxoandrosta-1,4-diene To a solution of 6α,9α-difluoro-11β-hydroxy-16α-methyl-17α-propionyloxy-3-oxoandrosta-1,4-diene-17β-carboxylic acid (100 g) in methyl ethyl ketone (500 mL), thiocarbornyl chloride (49.2 g), triethyl amine (67 g) and sodium iodide (3.3 g) were charged. The reaction mixture was heated to 70-75° C. for 2 hrs. After the completion of reaction, it was cool down to ambient temperature and the solid mass was filtered and washed with methyl ethyl ketone. The solid material was slurred in water and stirred for 30 min, filtered and washed with water till neutral pH of washings. Dried at 70-75° C. Yield: 92 g (77%), Purity: 92%.

EXAMPLE-5

17β-[(N,N-Dimethylcarbornyl)thio]-6α,9α-difluoro-11β-hydroxy-16α-methyl-17α-propionyloxy-3-oxoandrosta-1,4-diene To a solution of 6α,9α-difluoro-11β-hydroxy-16α-methyl-17α-propionyloxy-3-oxoandrosta-1,4-diene-17β-carboxylic acid (100 g) in acetone (500 mL), thiocarbornyl chloride (49.2 g), triethyl amine (67 g) and sodium iodide (3.3 g) were charged. The reaction mixture was heated to 70-75° C. for 6 hrs. It was cool down to ambient temperature and the solid mass was filtered and washed with acetone. The solid material was slurred in water and stirred for 30 min, filtered and washed with water till neutral pH of washings. Dried at 70-75° C. Yield: 84 g (70%), Purity: 94%.

EXAMPLE-6

17β-[(N,N-Dimethylcarbornyl)thio]-6α,9α-difluoro-11β-hydroxy-16α-methyl-17α-propionyloxy-3-oxoandrosta-1,4-diene To a solution of 6α,9α-difluoro-11β-hydroxy-16α-methyl-17α-propionyloxy-3-oxoandrosta-1,4-diene-17β-carboxylic acid (100 g) in THF (500 mL), thiocarbornyl chloride (49.2 g), triethyl amine (67 g) and sodium iodide (3.3 g) were charged. The reaction mixture was heated to 70-75° C. for 4 hrs. It was cool down to ambient temperature and the solid mass was filtered and washed with THF. The solid material was slurred in water and stirred for 30 min, filtered and washed with water till neutral pH of washings. Dried at 70-75° C. Yield: 100 g (92%), Purity: 90%.

EXAMPLE-7

6α,9α-difluoro-11β-hydroxy-16α[-methyl-17α-propionyloxy-3-oxoandrosta-1,4-diene-17β-carbothioc acid A suspension of 17β-[(N,N-dimethylcarbornyl)thio]-6α,9α-difluoro-11β-hydroxy-16α-methyl-17α-propionyloxy-3-oxoandrosta-1,4-diene (100 g) in morpholine (250 mL) was stirred at ambient temperature for 3 hrs. The reaction mass was added to a mixture of water, methyl ethyl ketone, toluene, and ethyl acetate at 10-15° C. To the reaction mass conc. HCl was added drop wise in 30 min at 10-15° C. till pH 1-2 was achieved. The precipitated solid mass was filtered, washed with water till get neutral pH of washings, and dried at 60-70° C. Yield 82 g (95%), Purity: 93%.

EXAMPLE-8

General Procedure for 6α,9α-difluoro-11β-hydroxy-16α[-methyl-17α-propionyloxy-3-oxoandrosta-1,4-diene-17β-carbothioc acid in Various Solvents Systems and in Different Bases A suspension of 17β-[(N,N-dimethylcarbornyl)thio]-6α, 9α-difluoro-11β-hydroxy-16α-methyl-17α-propionyloxy-3-oxoandrosta-1,4-diene (100 g) in appropriate solvents (2.5 volumes) optionally in the presences of a suitable base (2.2 mole eq.) was stirred at ambient temperature for 3 hrs. The reaction mass was added to a mixture of water methyl ethyl ketone, toluene and ethyl acetate at 10-15° C. To the reaction mass conc. HCl was added drop wise in 30 min at 10-15° C. till pH 1-2 was achieved. The precipitated solid mass was filtered, washed with water till get neutral pH of washings, and dried at 60-70° C. Effect of various solvents systems and in different bases over yield and quality of the product is mentioned in Experimental Table—1.

EXPERIMENTAL TABLE - 1

| Example No. | Base | Solvent | HPLC Purity | Yield | Temp ° C. |
|---|---|---|---|---|---|
| 9 | $K_2CO_3$ | Methanol | 76% | 55% | 50 |
| 10 | NaSH | Dimethyl acetamide | 80% | 80% | 75 |
| 11 | Diethyl amine | Dimethyl acetamide | 77% | 85% | 75 |
| 12 | Diethanol amine | Dimethyl acetamide | 80% | 67% | 75 |
| 13 | Morpholine | N-methyl piperidine | 72% | 82% | 80 |
| 14 | Piperidine | N-methyl piperidine | 69% | 78% | 80 |
| 15 | Morpholine | Ethyl acetate | 59% | 74% | 50 |
| 16 | Morpholine | | 93% | 80% | 25-30 |
| 17 | Pyrrolidine | | 73% | 80% | 50 |
| 18 | Diethanol amine | | 78% | 73% | 50 |

EXAMPLE-19

Purification of 6α,9α-difluoro-11β-hydroxy-16α[-methyl-17α-propionyloxy-3-oxoandrosta-1,4-diene-17β-carbothioc acid 6α,9α-Difluoro-11β-hydroxy-16α-methyl-17α-propionyloxy-3-oxoandrosta-1,4-diene-17β-carbothioc acid (100 g) is heated at 50-55° C. in a mixture of methyl ethyl ketone: toluene:ethyl acetate (1:1:1) stirred for 30 minutes. The slurry was cool down to ambient temperature and stirred for 1 hr. Solid mass was filtered and, washed with mixture of methyl ethyl ketone:toluene:ethyl acetate (1:1:1), and dried at 70-80° C. to give 86 g of product. Yield: 86%, HPLC Purity: 96%.

EXAMPLE-20

S-Fluoro methyl-6α,9α-difluoro-11β-hydroxy-16α-methyl-17α-propionyloxy-3-oxoandrosta-1,4-diene-17β-carbothioate (Fluticasone propionate)

To a suspension of potassium carbonate (57 g) in acetone (1000 mL), 6α,9α-difluoro-11β-hydroxy-16α[-methyl-17α- propionyloxy-3-oxoandrosta-1,4-diene-17β-carbothioc acid (100 g) was charged at ambient temperature and stirred for 30 minutes. The reaction mass was cool down to 0-5° C. and bromofluoromethane (36.2 g) gas was purged to reaction mass with regular intervals maintaining temperature of the reaction mass to 0-5° C. and further stirred for 2 hrs. After the completion of reaction, water (500 mL) was added too it and further stirred for next 1 hr. The solid mass from the reaction mixture was filtered and washed with a mixture of acetone:water (1:1). The wet solid mass was slurred with water and stirred for 1 hr. Solid product was filtered, washed with water till get neutral pH of washings, and dried at 70-75° C. Yield: 85 g (80%), HPLC Purity: 99%.

EXAMPLE-21

S-Fluoromethyl-6α,9α-difluoro-11β-hydroxy-16α-methyl-17α-propionyloxy-3-oxoandrosta-1,4-diene-17β-carbothioate (Fluticasone propionate)

To a suspension of potassium carbonate (28 g) in acetone (1000 mL), 6α,9α-difluoro-11β-hydroxy-16α[-methyl-17α-propionyloxy-3-oxoandrosta-1,4-diene-17β-carbothioc acid (100 g) was charged at ambient temperature and stirred for 30 minutes. The reaction mass was cool down to 0-5° C. and bromofluoromethane (25 g) gas was purged to reaction mass with regular intervals maintaining temperature of the reaction mass to 0-5° C. and further stirred for 2 hrs. After the completion of reaction, water (2000 mL) was added too it and further stirred for next 1 hr. The solid mass from the reaction mixture was filtered and washed with a mixture of acetone:water (1:1). The wet solid mass was slurred with water and stirred for 1 hr. Solid product was filtered, washed with water till get neutral pH of washings, and dried at 70-75° C. Yield: 92 g (87%), HPLC Purity: 94%.

EXAMPLE-22

S-Fluoromethyl-6α,9α-difluoro-11β-hydroxy-16α-methyl-17α-propionyloxy-3-oxoandrosta-1,4-diene-17β-carbothioate (Fluticasone propionate)

To a suspension of Triethyl amine (28 g) in acetone (1000 mL), 6α,9α-difluoro-11β-hydroxy-16α[-methyl-17α-propionyloxy-3-oxoandrosta-1,4-diene-17β-carbothioc acid (100 g) was charged at ambient temperature and stirred for 30 minutes. The reaction mass was cool down to 0-5° C. and bromofluoromethane (25 g) gas was purged to reaction mass with regular intervals maintaining temperature of the reaction mass to 0-5° C. and further stirred for 2 hrs. After the completion of reaction, water (2000 mL) was added too it and further stirred for next 1 hr. The solid mass from the reaction mixture was filtered and washed with a mixture of acetone:water (1:1). The wet solid mass was slurred with water and stirred for 1 hr. Solid product was filtered, washed with water till get neutral pH of washings, and dried at 70-75° C. Yield: 92 g (87%), HPLC Purity: 94%.

EXAMPLE-23

Purification of Fluticasone Propionate

A suspension of fluticasone propionate (100 g) in acetone (300 mL) was stirred at 50-55° C. for 30 minutes. The solution was cool down to 25-30° C. and stirred for 1 hr. The solid mass was filtered, washed with acetone (100 mL) and dried to get 90 g of pure fluticasone propionate (HPLC Purity>99.5%).

EXAMPLE-24

Purification of Fluticasone Propionate

A solution of fluticasone propionate (100 g) in acetone (3 L) was stirred at 45-55° C. to get almost clear solution then filtered through hyflow bed over a fine filter bed (5µ) at 45-55° C. Approximately 2.7 L acetone was distilled out from the solution and filtered water was added to the solution. The solid obtained was filtered, washed with water and dried to get 95 g of pure fluticasone propionate (HPLC Purity>99.5%).

EXAMPLE-25

6α,9α-Difluoro-11β-hydroxy-16α-methyl-17α-(2-furoyloxy)-3-oxoandrosta-1,4-diene-17β-carboxylic acid A suspension of 6α,9α[-difluoro-11β,17α-dihydroxy-16α-methyl-3-oxoandrosta-1,4-diene-17β-carboxylic acid (100 g) and triethyl amine (58.6 g) in acetone (500 mL) was cooled to 0-5° C., Another solution of furoyl chloride (92.5 g) in acetone (100 mL) was added to it very slowly in 1 hr and the reaction mixture was further stirred for 2 hr at 0-5° C. The reaction mixture was warmed up to 40-45° C. and diethyl amine (36.86 g) was added drop wise with in 30 minutes. The reaction mixture was further stirred for 2 hr at 40-45° C., then cool down to 20-25° C. To the reaction mixture water was added slowly for 30 minutes and the reaction mixture was acidified to pH 1.5-2.0 by the addition of conc. HCl and further stirred for 45 min. The precipitated solid product is filtered, washed with water, and dried at 70-75° C. Yield: 125 gm (99.00%), HPLC Purity: 97%.

EXAMPLE-26

17β-[(N,N-Dimethylcarbornyl)thio]-6α,9α-difluoro-11β-hydroxy-16α-methyl-17α-(2-furoyloxy)-3-oxoandrosta-1,4-diene To a solution of 6α,9α-difluoro-11β-hydroxy-16α-methyl-17α-(2-furoyloxy)-3-oxoandrosta-1,4-diene-17β-carboxylic acid (100 g) in methyl ethyl ketone (500 mL), thiocarbornyl chloride (49.2 g), triethyl amine (67 g) and sodium iodide (3.3 g) were charged. The reaction mixture was heated to 70-75° C. for 2 hrs. After the completion of reaction, it was cool down to ambient temperature and the solid mass was filtered and washed with methyl ethyl ketone. The solid material was slurred in water and stirred for 30 min, filtered and washed with water till neutral pH of washings. Dried at 70-75° C. Yield: 98 g (78%), Purity: 92%.

EXAMPLE-27

6α,9α-Difluoro-11β-hydroxy-16α[-methyl-17α-(2-furoyloxy)-3-oxoandrosta-1,4-diene-17β-carbothioc acid A suspension of 17β-[(N,N-dimethylcarbornyl)thio]-6α, 9α-difluoro-11β-hydroxy-16α-methyl-17α-(2-furoyloxy)-3-oxoandrosta-1,4-diene (100 g) in morpholine (250 g) was stirred at ambient temperature for 4 hrs. The reaction mass was added to a mixture of water and ethyl acetate at 10-15° C.

Glacial acetic acid (170 mL) was added drop wise in 30 min in the reaction mass at 10-15° C. to get pH 5-7. The precipitated solid mass was filtered, washed with water till get neutral pH of washings, and dried at 60-70° C. Yield: 81 g (92%), Purity: 90%.

EXAMPLE-28

6α,9α-Difluoro-11β-hydroxy-16α[-methyl-17α-(2-furoyloxy)-3-oxoandrosta-1,4-diene-17β-carbothioc acid 6α,9α-Difluoro-11β-hydroxy-16α[-methyl-17α-(2-furoyloxy)-3-oxoandrosta-1,4-diene-17β-carbothioc acid (100 g) is heated at 50-55° C. in ethyl acetate (300 mL) stirred for 30 minutes. The slurry was cool down to ambient temperature and stirred for 1 hr. Solid mass was filtered and, washed with mixture of ethyl acetate, and dried at 70-80° C. to give 80 g of product. Yield: 80%, HPLC>Purity 96%.

EXAMPLE-29

S-Fluoromethyl-6α,9α-difluoro-11β-hydroxy-16α-methyl-17α-(2-furoyloxy)-3-oxoandrosta-1,4-diene-17β-carbothioate (Fluticasone furoate)

To a solution of 6α,9α-difluoro-11β-hydroxy-16α[-methyl-17α-(2-furoyloxy)-3-oxoandrosta-1,4-diene-17β-carbothioc acid (100 g) in acetone (1000 mL), another solution of potassium carbonate (57 g) and water (150 mL) was added drop wise in 30 minutes. The reaction mass was cool down to 0-5° C. and bromofluoromethane (33.2 g) gas was purged to reaction mass with regular intervals for 30 minutes maintaining temperature of the reaction mass to 0-5° C. and further stirred for 2 hrs. After the completion of reaction, water was added too it and further stirred for next 20 minutes. The solid mass from the reaction mixture was filtered and washed with acetone (100 mL). The solid mass was slurred with water and stirred for 1 hr. Solid product was filtered, washed with water till get neutral pH of washings, and dried at 70-75° C. Yield: 92 g (87%), HPLC Purity: 94%.

EXAMPLE-30

Purification of Fluticasone Furoate

A mixture of fluticasone furoate (100 g) and methyl ethyl ketone (300 mL) was stirred at 50-55° C. for 30 minutes. The solution was cooled down to down to 25-30° C. and stirred for 1 hr. The solid mass was filtered, washed with methyl ethyl ketone, and dried at 70-80° C. Yield: 80 g (80%), Purity>99%.

EXAMPLE-31

Purification of Fluticasone Furoate

A solution of fluticasone furoate (100 g) in ethyl acetate (3 L) was stirred at 45-55° C. to get almost clear solution, and then filtered through hyflow bed over a fine filter bed (5μ) at 45-55° C. Approximately 2.7 L ethyl acetate was distilled out from the solution and filtered water was added to the solution. The solid obtained was filtered, washed with water and dried to get 95 g of pure product (HPLC Purity>99.5%).

We claim:
1. A process for the preparation of compound of Formula 1, comprising

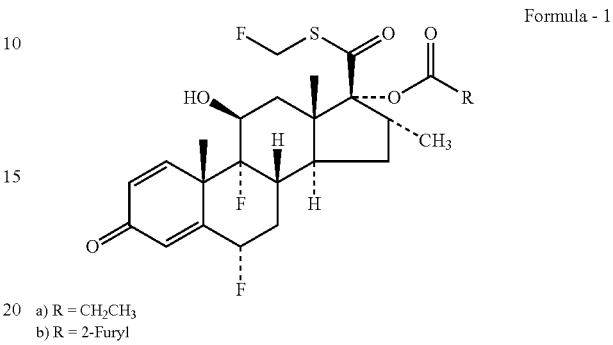

Formula - 1
a) R = CH$_2$CH$_3$
b) R = 2-Furyl i) reacting the compound of formula 5 (wherein R=CH$_2$CH$_3$ or 2-furyl) with suitable cyclic amine to obtain the compound of formula 6 (wherein R=CH$_2$CH$_3$ or 2-furyl);

Formula-5
a) R = CH$_2$CH$_3$
b) R = 2-Furyl

Formula-6
a) R = CH$_2$CH$_3$
b) R = 2-Furyl ii) purifying the compound of formula 6 (wherein R=CH$_2$CH$_3$ or 2-furyl) using suitable solvents or mixture thereof;
iii) reacting the compound of formula 6 (wherein R=CH$_2$CH$_3$ or 2-furyl) with bromofluoromethane in a suitable solvent and in presence of suitable base to obtain the compound of formula 1 (wherein R=CH$_2$CH$_3$ or 2-furyl);

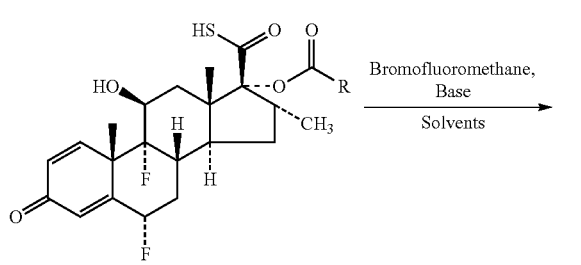

Formula-6
a) R = CH₂CH₃
b) R = 2-Furyl

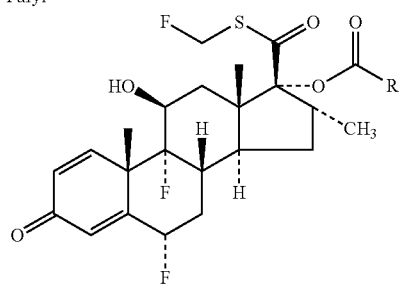

Formula-1
a) R = CH₂CH₃
b) R = 2-Furyl iv) optionally purifying the compound of the formula 1 (wherein R=CH$_2$CH$_3$ or 2-furyl) using suitable solvents or mixture thereof.

2. The process according to claim 1 step (i), wherein the suitable cyclic amines are selected from morpholine, piperidine, pyrollidine and pyridine either independently or in suitable mixture thereof.

3. The process according to claim 1 step (ii), wherein the suitable solvent(s) for the purification is selected from suitable hydrocarbons, esters and ketones either independently or in suitable mixture thereof.

4. The process according to claim 1 step (iii), wherein the suitable solvent(s) is selected from ketones, nitriles and (C$_1$ to C$_{10}$) linear or branched chain alcohols.

5. The process according to claim 1 step (iii), wherein the suitable base is selected from suitable inorganic bases and suitable cyclized and non-cyclised organic bases.

6. The process according to claim 5, wherein the suitable inorganic bases are selected from carbonates, bicarbonates and hydroxides.

7. The process according to claim 1 step (iv), wherein the suitable solvent(s) is selected from esters, halogenated hydrocarbon solvents, ketones, amides, (C$_1$ to C$_{10}$) linear or branched chain alcohols.

* * * * *